(12) United States Patent
Lagneaux et al.

(10) Patent No.: US 6,179,275 B1
(45) Date of Patent: Jan. 30, 2001

(54) DYNAMIC SPRAYER FOR AN ODORIFEROUS SUBSTANCE WITH LOW ENERGY CONSUMPTION

(75) Inventors: Patrick Lagneaux, Onnaing; Christian Peretti, Valenciennes, both of (FR)

(73) Assignee: Prodifa, Valenciennes (FR)

( * ) Notice: Under 35 U.S.C. 154(b), the term of this patent shall be extended for 0 days.

(21) Appl. No.: 09/202,669
(22) PCT Filed: Jun. 21, 1996
(86) PCT No.: PCT/FR96/00981
§ 371 Date: Dec. 18, 1998
§ 102(e) Date: Dec. 18, 1998
(87) PCT Pub. No.: WO97/49435
PCT Pub. Date: Dec. 31, 1997
(51) Int. Cl.[7] .................................................. B01F 3/04
(52) U.S. Cl. ............................ 261/30; 261/84; 261/104; 261/DIG. 65
(58) Field of Search ............................. 261/30, 84, 104, 261/83, DIG. 65

(56) References Cited

U.S. PATENT DOCUMENTS 4,035,451 * 7/1977 Tringali ............................... 261/101

* cited by examiner

*Primary Examiner*—Chester T. Barry
(74) *Attorney, Agent, or Firm*—Wolf, Greenfield & Sacks, P.C.

(57) ABSTRACT

The diffuser (1) includes a receptacle which contains the odorous substance to be diffused in liquid form or the like, and which is closed by a diffusion membrane (3c), and means for rotating the receptacle about itself. The receptacle includes a plurality of compartments which enable the weight of the odorous substance to be distributed over the periphery of the axis of rotation (DD) of the receptacle. In a preferred embodiment, the receptacle includes at least one annular-type housing (3) which is centered on the axis of rotation of the receptacle, and which is partitioned into a plurality of identical compartments (5a, 5b, 5c, 5d, 5e, 5f).

7 Claims, 3 Drawing Sheets

DYNAMIC SPRAYER FOR AN ODORIFEROUS SUBSTANCE WITH LOW ENERGY CONSUMPTION

Figure 1:
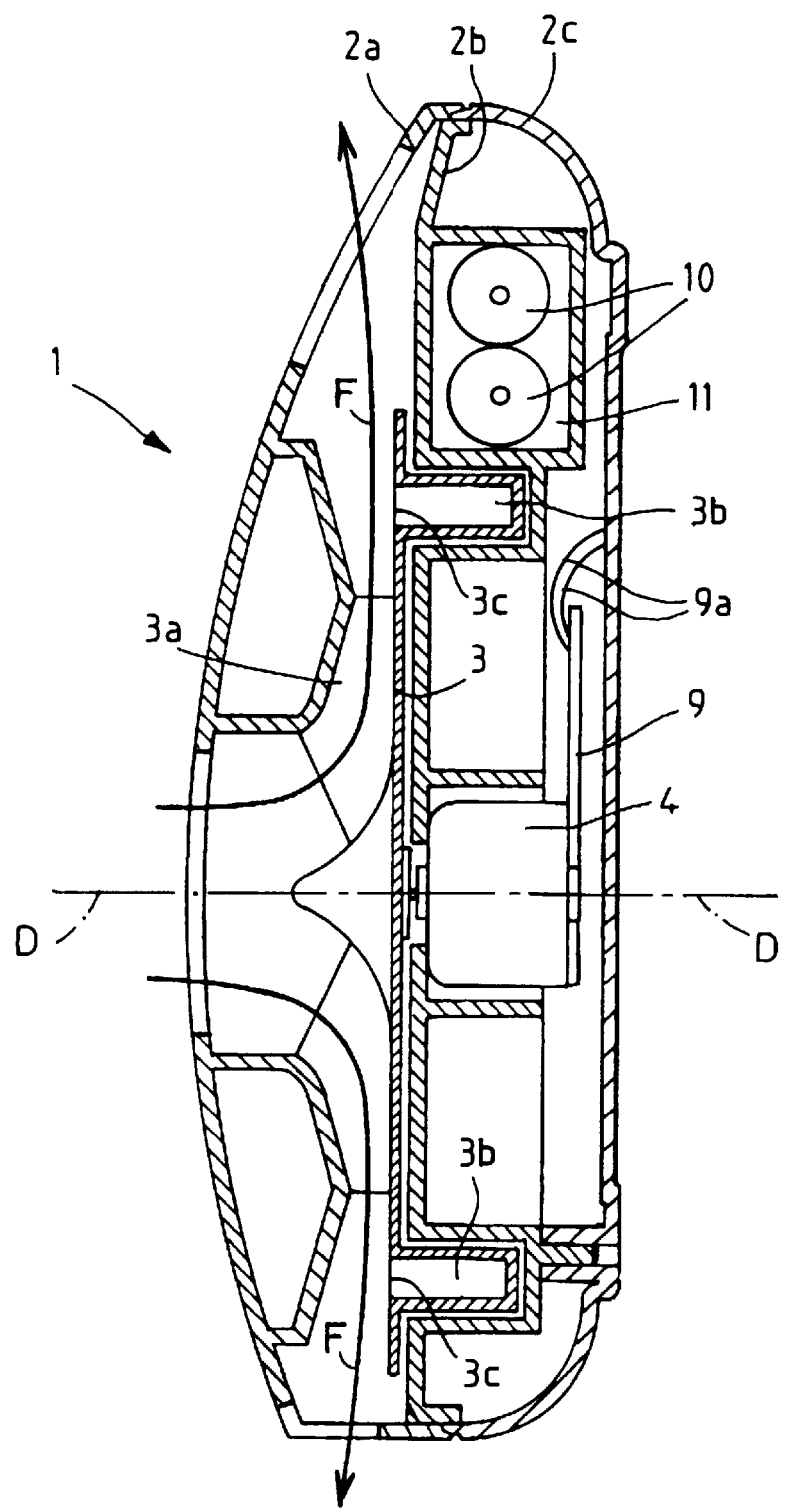

The present invention relates to a dynamic fragrance diffuser, in which the odorous substance that is to be diffused into the atmosphere is contained in a receptacle which is closed by a diffusion membrane and which is rotated about its own axis. It relates more particularly to an improved dynamic diffuser which enables the amount of energy required to rotate the receptacle to be minimized. In the present text, the term "odorous substance" is used to designate any substance which diffuses naturally into the atmosphere, e.g. air freshener, insecticide, germicide, . . . , and which can move inside the receptacle. It could, for example, be a liquid substance or even a substance that is presented in the form of beads or granules.

A dynamic fragrance diffuser has already been described in European patent application EP 672 425, for example. In a preferred embodiment, the diffuser consists of a housing which contains a removable autonomous cartridge and which can be rotated about its own axis by means of a motor. The autonomous cartridge consists, more particularly, of a circular plate whose periphery forms an annular housing which is centered on the axis of rotation of the cartridge and which is closed by a diffusion membrane. The annular housing contains the odorous substance which is to be diffused into the atmosphere. More particularly, the odorous substance is a liquid substance, and the diffusion membrane is designed to be permeable to gas and impermeable to liquid.

In accordance with the teaching of European patent application EP 672 425, when the fragrance diffuser is in a position such that the cartridge is not in a horizontal plane, when said cartridge is rotated, the odorous substance, which can move inside the annular housing under the effect of its own weight, remains confined to the bottom portion of said housing. As a result, rotation of the cartridge enables the diffusion membrane to be brought into contact with the odorous substance. It can thus be understood that on each revolution of the cartridge, the entire surface of the diffusion membrane is brought into contact with the odorous substance, whatever the quantity of substance in the annular housing. When using a liquid substance for example, the entire surface of the diffusion membrane is thus impregnated on each revolution until almost all of the odorous liquid substance has run out.

In practice, the motor which rotates the cartridge is a low-powered DC motor which is powered cordlessly by means of batteries housed in the housing. Unfortunately, it can be observed, by operating the dynamic fragrance diffuser of European patent application EP 672 425, that the consumption of the DC motor is relatively high, and leads rapidly to the batteries powering said motor wearing out prematurely.

The object of the present invention is thus to propose a dynamic diffuser for diffusing an odorous substance of liquid type or the like, which has the advantage of the above-mentioned diffuser in that it enables the entire surface of the diffusion membrane to be put into contact with the odorous substance, whatever the quantity of odorous substance, but which mitigates the main drawback in that it draws much less power in operation.

This object is achieved completely by the dynamic diffuser of the invention which, in a manner that is known, in particular from European patent application EP 672 425, comprises, firstly, a receptacle which contains an odorous substance in liquid form or the like, i.e. an odorous substance that is capable of being moved inside the receptacle under the effect of its own weight, and which is closed by a diffusion membrane, and secondly, means for rotating the receptacle about its own axis.

In a manner characteristic of the invention, the receptacle includes a plurality of compartments which enable the weight of the odorous substance to be distribution over the periphery of the axis of rotation of the receptacle.

In the diffuser of the invention, and in contrast to the diffuser of European patent application EP 672 425, the odorous substance contained in each compartment is rotated. As a result, on each revolution of the receptacle, the odorous substance contained in a compartment is brought, under the combined effect of the rotation and its own weight, into contact with the entire surface of the portion of the membrane locally closing said compartment, whatever the quantity of substance contained in the compartment. With regard to impregnating the diffusion membrane, the same overall result is obtained for the set of compartments as that which is obtained for the fragrance diffuser of European patent application EP 672 425. However, given that the odorous substance is distributed over the periphery of the axis of rotation of the receptacle, the unbalance phenomenon which is inherent in prior art diffusers is avoided, said phenomenon resulting in the weight of the odorous substance remaining localized in the bottom portion of the receptacle, and constantly opposing rotation of the receptacle about its own axis. The amount of power required to rotate the receptacle of the diffuser of the invention is therefore much less.

Advantageously, the compartments of the receptacle are identical, and diametrically opposite in pairs about the axis of rotation of the receptacle.

In a preferred variant embodiment, the receptacle includes at least one annular-type housing which is centered on the axis of rotation, and which is partitioned into a plurality of identical compartments. Here, the term "an annular-type housing" is used to designate any type of closed ring. It could, for example, be a ring forming a circle, or forming a polygon, such as an octagon, a hexagon, a square, etc.

The receptacle is advantageously rotated intermittently, thereby enabling power consumption to be limited in time. The cartridge is rotated intermittently by means of a photoelectric cell for example, as a function of the light level.

Figure 2:
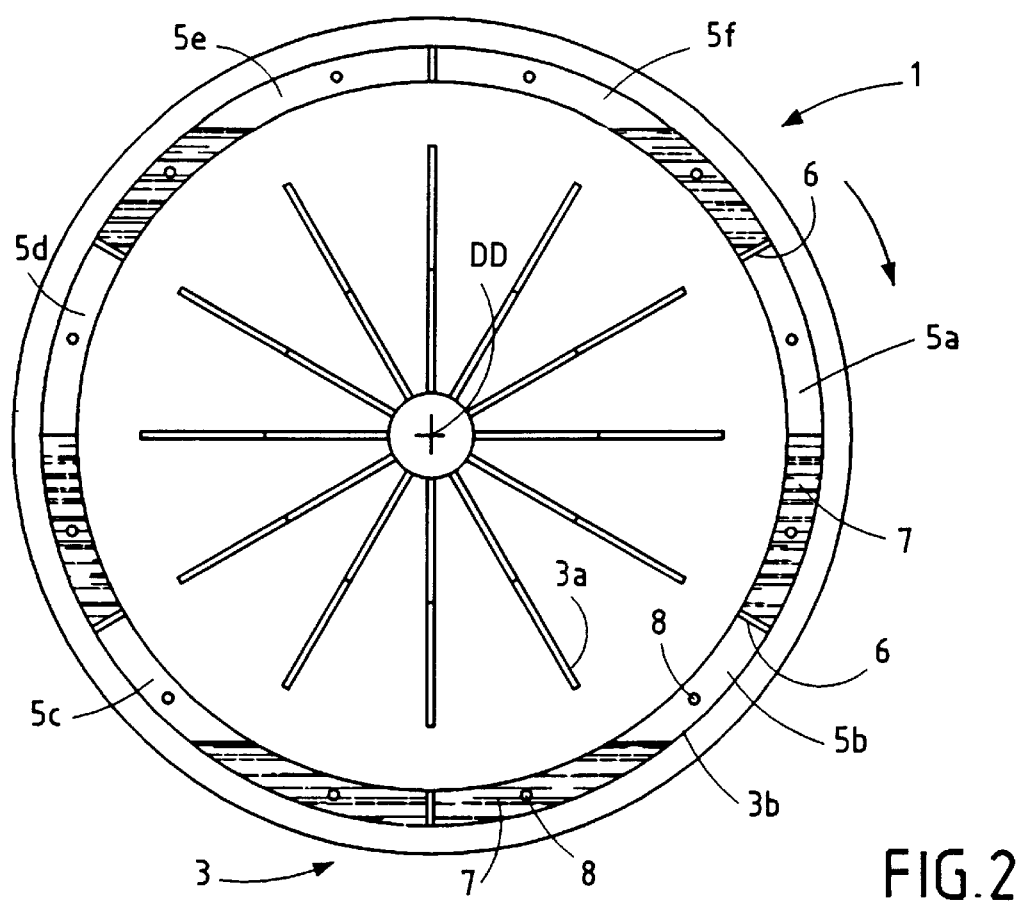
Figure 3:
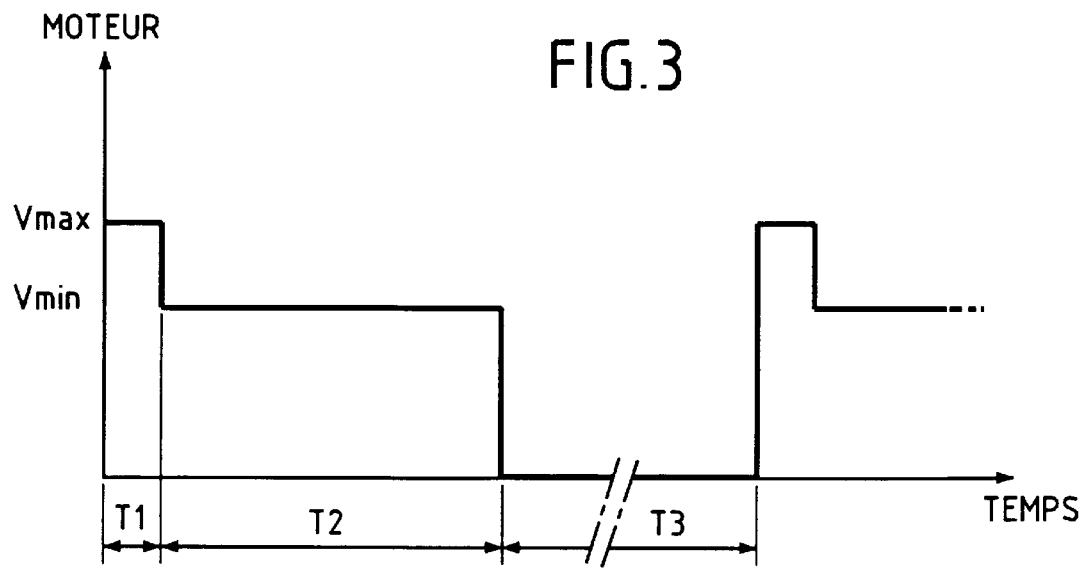
Figure 4:
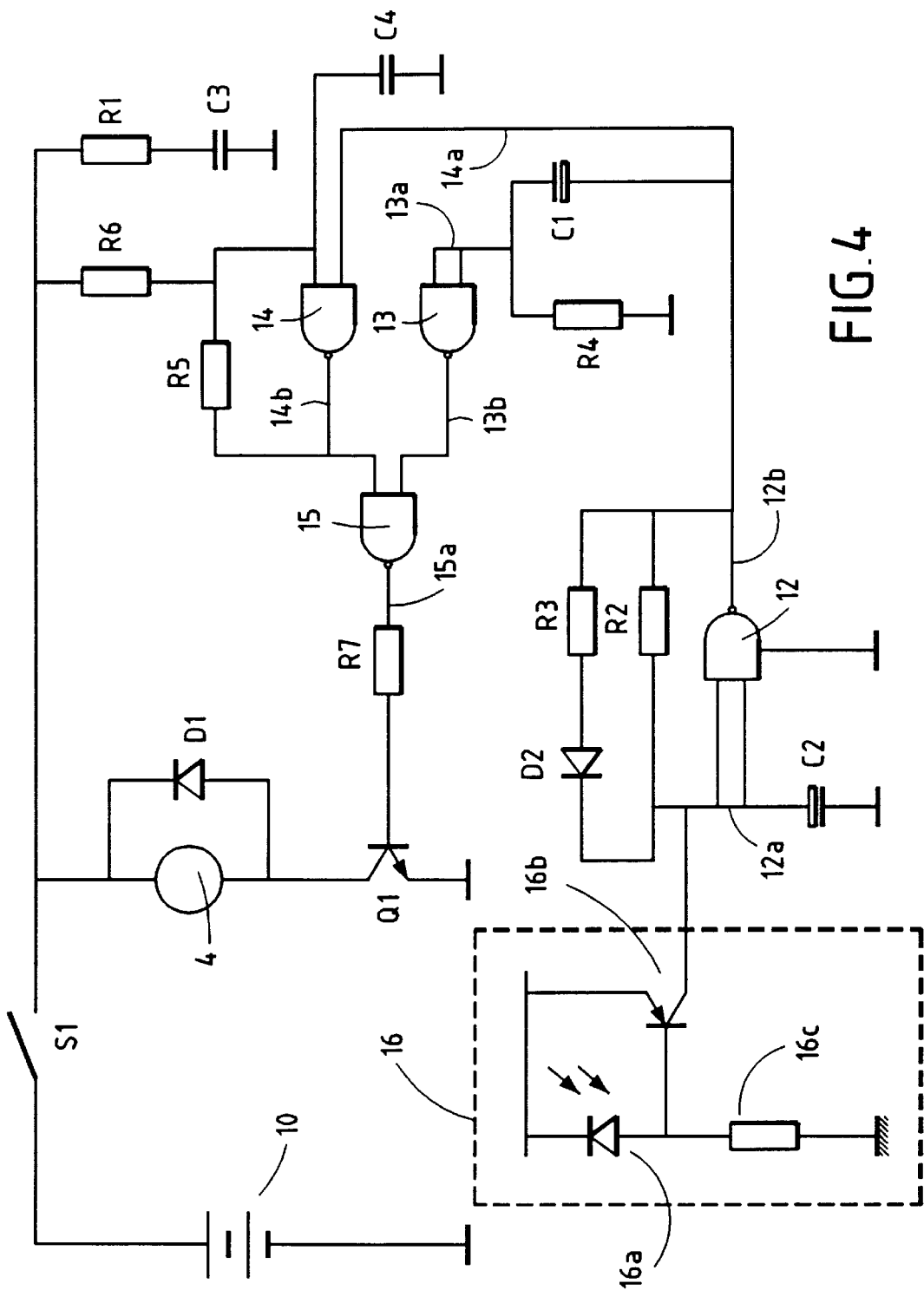

Other characteristics and advantages of the invention appear more clearly on reading the following description of a preferred embodiment of a dynamic fragrance diffuser of the invention, which description is given by way of non-limiting example and with reference to the accompanying drawings, in which:

FIG. 1 is a section view of a dynamic fragrance diffuser of the invention which is fitted with a removable cartridge that is rotated about axis DD by means of a DC motor;

FIG. 2 if a front view of the removable cartridge of the fragrance diffuser of FIG. 1;

FIG. 3 shows the cycle, in terms of time, for controlling the power supply voltage to the DC motor of the diffuser of FIG. 1; and FIG. 4 shows the electronic circuit diagram of the circuit for controlling the DC motor of the diffuser of FIG. 1.

With reference to FIG. 1, the dynamic fragrance diffuser 1 comprises a housing made up of three portions: a front portion 2*a*; a rear portion 2*c*; and a middle portion 2*b*; which housing serves in particular as a support for a removable cartridge 3. The cartridge 3 comprises an annular housing 3*b* containing the odorous substance to be diffused, and is rotated about an axis DD by means of a DC motor 4.

The fragrance diffuser of FIG. 1 differs from the diffuser described in European patent application EP 672 425 and shown in FIG. 2 of said application, only by the particular shape of its annular housing 3b which is described below with reference to FIG. 2, and by the intermittent control cycle of the DC motor 4 which is shown in FIG. 3. All the other structural elements of the two diffusers, and the way in which they operate to create and diffuse a flow of air F under the effect of the cartridge 3 rotating, are identical, and are therefore not described in detail in the present description. It suffices to refer to the text of European patent application EP 672 425, corresponding to U.S. Pat. No. 5,480,591, which is specifically hereby incorporated by reference, and whose teaching forms an integral part of the present description. It is merely recalled that the removable cartridge 3 is substantially disk-shaped and is provided on one of its faces with diffusion blades 3a. Its annular housing 3b which contains the odorous substance to be diffused is circular, is centered on the axis of rotation DD, and is closed by a diffusion membrane 3c which is permeable to gas, but impermeable to liquid.

In the invention, with reference to FIG. 2, the annular housing 3b of the removable cartridge 3 is subdivided by partitions 6 into six compartments 5a, 5b, 5c, 5d, 5e, 5f which are sealed and contiguous. The six compartments are identical, and diametrically opposite in pairs about the axis of rotation of the removable cartridge 3.

In the example shown, each compartment 5a to 5f contains an odorous substance 7 in liquid form. Once the diffusion membrane 3c has been put into place, the odorous substance is inserted into each compartment 5a to 5f by means of insertion orifices 8 provided in the bottom of each compartment. Once the substance has been inserted into a compartment, the orifices 8 are closed using any appropriate means. For a cartridge made of plastics material for example, and in particular made of polypropylene, the orifices 8 are closed by heat-sealing for example, after the substance has been inserted.

Before the removable cartridge is used, each compartment 5a to 5f is initially three-quarters full of odorous substance. FIG. 2 shows a cartridge while it is in use, with a portion of the odorous substance that was initially contained in each compartment having already been diffused through the membrane 3c.

According to the invention, when the cartridge 3 is rotated about the axis DD by means of the DC motor 4, the liquid substance 7 contained in each compartment is itself caused to rotate. When the cartridge 3 rotates through 360° and under the combined effects of the liquid's own weight and of the rotation imparted thereto by the cartridge 3 as a result of the presence of the partitions 6, the liquid substance 7 contained in each compartment comes into contact with the entire surface of the diffusion membrane 3c in the corresponding compartment, whatever the volume of liquid substance in a given compartment. Thus, each time the cartridge 3 rotates, the diffusion membrane 3c is completely impregnated on its entire surface by the liquid substance contained in the set of compartments 5a to 5f until the odorous liquid substance has run out completely or almost completely.

To obtain the above-mentioned technical effect with regard to impregnating the diffusion membrane 3c, it suffices that the odorous substance can be moved under the effect of its own weight inside its compartment. That technical effect is consequently obtained not only when the fragrance diffuser is positioned so that the axis of rotation DD is horizontal, as shown in FIG. 1, but also for any position of the fragrance diffuser in which the axis DD is inclined relative to the horizontal. In addition, it is not necessary in the context of the invention for the odorous substance to be presented in liquid form. It suffices that the odorous substance is capable of being moved inside the receptacle. Consequently, the odorous substance may also be presented in particulate form, and in particular in the form of microbeads. In this case, it is also not necessary for the diffusion membrane 3c to be impermeable to liquid; it suffices that it is permeable to gas.

Compared with the cartridge of the diffuser described in European patent application EP 672 425, the cartridge of FIG. 2 has the additional advantage of being capable of being put into rotation and kept rotating using much less energy. The mass of liquid to be diffused is distributed over the entire periphery of the axis of rotation DD, thereby mitigating the unbalance phenomenon which is inherent in the diffuser of European patent application EP 672 425 and which is the cause of the high electricity consumption of its DC motor. In addition, in the preferred embodiment of FIG. 2, said distribution of the mass of substance to be diffused is performed evenly since the annular housing 3 is centered on the axis of rotation DD, and since the compartments 5a to 5f are all identical and diametrically opposite in pairs about the axis DD. This results in minimum electricity consumption compared with other possible variant embodiments of the invention in which distribution is uneven. Naturally, in the context of the preferred variant embodiment of FIG. 2, the cartridge may include a plurality of annular housings that are concentric about the axis DD.

Due to the compartmented structure of the annular housing 3b of the cartridge in FIG. 2, it is possible to rotate said cartridge intermittently without any risk of excessive electricity consumption, unlike the cartridge of the diffuser of European patent application EP 672 425 in which the unbalance phenomenon predominates whenever the cartridge starts to rotate.

With reference to FIG. 1, the DC motor 4 is powered by means of an electronic control circuit 9, which is itself connected by two feed wires 9a to two batteries 10 which are disposed inside a housing 11 that is provided in the middle portion 2b of the diffuser housing. A switch (not shown) is preferably provided on one of the two feed wires 9a and projects onto the facade of the middle portion 2b.

In a particular embodiment, the electronic control circuit 9 is designed to control the DC motor 4 in application of the intermittent cycle shown in FIG. 3, for the purpose of increasing the lifetime of the batteries 10 compared with rotating the cartridge continuously. In this particular cycle, the motor is powered at start-up at a constant maximum voltage $V_{max}$ for a duration $T_1$ corresponding to setting the cartridge into rotation. At the end of the first or starting stage, the DC motor 4 is powered during a second stage of duration $T_2$ at a constant minimum voltage $V_{min}$, which is selected to be at least sufficient, and preferably to be only just sufficient to maintain the rotary motion of the cartridge, thereby enabling power consumption to be limited. Finally, in a third stage of duration $T_3$, the DC motor 4 is no longer powered. At the end of the second stage $T_2$, the speed of rotation of the cartridge rapidly decreases to become zero. At the end of the third stage $T_3$, the three-stage cycle described above is repeated.

In a particular embodiment, the durations $T_1$, $T_2$, and $T_3$ of the three stages of the cycle are respectively about 8 seconds, 42 seconds, and 90 seconds.

FIG. 4, which is described below, shows a particular embodiment of the electronic control circuit 9 that enables the DC motor to be powered with the cycle of FIG. 3. Other embodiments known to the person skilled in the art can naturally be envisaged, with a view to implementing the particular control cycle of FIG. 3.

The electronic architecture of the circuit in FIG. 4 is based on the use of four inverting logic AND gates, referenced 12, 13, 14, and 15, and more commonly referred to as NAND gates. The circuit of FIG. 4 operates as follows. When the switch S1 is closed, the input 12a of gate 12 is in a low state, and its output 12b is in a high state. This high state is applied to the input 13a of gate 13 via capacitor C1. As a result, the output 13b of gate 13 is in a low state, and as a result the output 15a of gate 15 is in a high state. The transistor $Q_1$ is therefore conductive, and the DC motor 4 is powered at a maximum voltage $V_{max}$ corresponding to the power supply voltage supplied by the batteries 10.

The DC motor 4 remains powered at said voltage $V_{max}$ throughout the time required for capacitor C1 to discharge through resistor R4, which discharge serves to determine the duration $T_1$.

When capacitor C1 is discharged, the input 13a of gate 13 is at a low level, and as a result the output 13b of gate 13 is in a high state.

In association with resistor R5 and capacitor C4, gate 14 forms an oscillator and delivers an alternating output signal 14b so long as its input signal 14a is in a high state. In a particular embodiment, the frequency of the alternating signal 14b is 2500 HZ. The alternating output signal 14b is inverted at output 15b of gate 15, while the output 13b of gate 13 remains in a high state (duration $T_2$). During said period, the power supply voltage delivered by the batteries 10 is chopped at the frequency of the oscillator formed by gate 14, with transistor $Q_1$ being alternately conductive and nonconductive. As a result, the DC motor 4 is powered, on average, at a voltage $V_{min}$ which is less than the power supply voltage $V_{max}$ of the batteries 10, and which has a value that depends on the frequency of the output signal 15a of gate 15.

Throughout the period $T_2$, capacitor C2 is charged via resistor R3 in series with diode D2 and via resistor R2. When capacitor C2 is sufficiently charged, gate 12 switches over and its output 12b passes to a low state. As a result, the input 14a of gate 14 also passes to a low state. The oscillator formed by gate 14 is blocked, and the output 14b of gate 14 remains constantly in a high state. As a result, the output 15a of gate 15 passes to a low state, thereby blocking transistor $Q_1$. The DC motor 4 is no longer powered, thereby corresponding to the third stage of duration $T_3$. During this entire stage, capacitor C2 discharges through resistor R2 until the output 12b of gate 12 again switches over to a high state, thereby restarting the cycle.

With reference to FIG. 4, the electronic control circuit of the DC motor 4 for rotating the cartridge 3 includes, according to an additional characteristic, a photoelectric cell 16 which generally has the function of switching off the power supply to the DC motor 4 whenever the light level is below a certain threshold. The threshold corresponds to a night-time period for example, during which the cartridge is not rotated.

In the particular example of FIG. 4, when the light level is above the predetermined threshold, the photodiode 16a is conductive, and the transistor 16b is blocked. The diffuser functions in accordance with the above-mentioned normal cycle. When the light level passes below the threshold, the photodiode 16a is blocked and the transistor 16b enters into conduction because of the presence of the resistor 16c. The transistor 16b conducts while the light level remains below the threshold. The input 12a of logic gate 12 is thus forced into a low state so long as the light level does not return above the threshold, thereby interrupting the normal control cycle of the motor as described above, and as shown in FIG. 3.

The invention is not limited to the preferred embodiment described above with reference to FIGS. 1 to 4. In particular, intermittent control of the DC motor 4 is not limited to the particular cycle shown in FIG. 3. The motor could be under ON/OFF control using a first stage during which the motor is powered at a maximum voltage, and a second stage during which the motor is unpowered. In addition, the shape of the diffuser housing is not limited to that shown in FIG. 1 but could be different and, for example, it could be similar to that shown in FIG. 1 of European patent application EP 672 425. All the improvements of the diffuser of said European patent application could also be applied to the fragrance diffuser, in particular with regard to the use of an absorbent material in contact with the diffusion membrane. In the context of the invention, the cartridge is not necessarily removable, but could be fixed to reside in the housing of the fragrance diffuser. Such a cartridge would also not have to be provided with blades.

What is claimed is:

1. A dynamic diffuser for diffusing an odorous substance in liquid form, the diffuser including a receptacle which contains the odorous substance and which is closed by a diffusion membrane, and a motor structured to rotate the receptacle about an axis of rotation, the receptacle including a plurality of compartments which enable the weight of the odorous substance to be distributed over the periphery of the axis of rotation of the receptacle, each of the compartments containing a quantity of the liquid odorous substance, rotation of the receptacle about the axis of rotation causing the odorous substance to come in contact with the diffusion membrane.

2. The diffuser according to claim 1, wherein the compartments of the receptacle are all identical and are diametrically opposed in pairs about the axis of rotation of the receptacle.

3. The diffuser according to claim 1, wherein the receptacle includes at least one annular-type housing which is centered on the axis of rotation of the receptacle, and which is partitioned into a plurality of identical compartments.

4. The diffuser according to claim 1, wherein the motor is designed to rotate the receptacle intermittently.

5. The diffuser according to claim 4, wherein the the motor is a DC motor which is powered at a variable voltage, whose rotor is coupled to the axis of rotation of the receptacle, and whose power supply voltage is controlled to perform the following cycle:

a) in a starting, first stage, the motor is powered at a maximum voltage during a predetermined first duration;

b) in a second stage, the motor is powered during a predetermined second duration at a voltage that is lower than the maximum voltage but that is sufficient to sustain the rotary motion of the receptacle; and c) in a third stage, of a third duration, a power supply voltage of the motor is zero.

6. The diffuser according to claim 5, wherein the third duration of the third stage is about twice as long as the second duration of the second stage, which is about six times longer than the first duration of the first stage.

7. The diffuser according to claim 4, wherein the receptacle is rotated intermittently by means of a photoelectric cell as a function of a light level.

* * * * *